United States Patent [19]

Imamura et al.

[11] Patent Number: 4,525,458

[45] Date of Patent: Jun. 25, 1985

[54] METHOD FOR THE PRODUCTION OF SPHINGOMYELINASE

[75] Inventors: Shigeyuki Imamura; Hideo Misaki; Naoki Muto, all of Shizuoka, Japan

[73] Assignee: Toyo Jozo Company, Ltd., Shizuoka, Japan

[21] Appl. No.: 413,677

[22] Filed: Sep. 1, 1982

[30] Foreign Application Priority Data

Sep. 9, 1981 [JP] Japan ................................ 56-140902

[51] Int. Cl.³ .......................... C12N 9/16; C12R 1/465
[52] U.S. Cl. ..................................... 435/196; 435/886
[58] Field of Search ......................................... 435/196

[56] References Cited

U.S. PATENT DOCUMENTS 4,275,162  6/1981  Beppu et al. ........................ 435/196

Primary Examiner—Lionel M. Shapiro
Attorney, Agent, or Firm—Wyatt, Gerber, Shoup, Scobey and Badie

[57] ABSTRACT

The invention is to provide a method for the production of sphingomyelinase, by culturing in a medium a sphingomyelinase-producing strain belonging to genus Streptomyces and collecting the resulting sphingomyelinase from the cultured medium. The strain, Streptomyces sp. A 9107, newly separated from a soil, is found preferable for the method of the present invention, and has been deposited as NRRL 15100 and FERM-P 4978.

1 Claim, 3 Drawing Figures

METHOD FOR THE PRODUCTION OF SPHINGOMYELINASE

The present invention relates to a method for the production of sphingomyelinase by fermentation process and more particularly, to a method for the production of sphingomyelinase by culturing a sphingomyelinase-producing microorganisms belonging to genus Streptomyces in a medium and collecting the resulting sphingomyelinase from the culture product.

Hitherto, *Staphylococcus aureus* and *Bacillus cereus* have been known as sphingomyelinase-producing bacterias which act on sphingomyelin to produce ceramide and phosphorylcholine.

The present inventors have searched for microorganisms producing the foregoing sphingomyelinase, and found that, of soil microorganisms, Streptomyces sp. A 9107, a variety of *actimomycetes*, produces the enzyme of the present invention. The present inventors have thus accomplished the present invention.

Streptomyces sp. A 9107 is a strain separated from the soil of a radish field in Heda Mura, Tagata Gun, Shizuoka Prefecture, Japan, and its mycological characteristics are as follows:

(I) FORM

Naked-eye observation shows that the aerial mycelium having ripe spores is brown to gray, and that the substrate mycelium is yellow to yellowish brown and produces no soluble coloring matters.

The results of observation after culture in starch-inorganic salt-agar media at 30° C. for 10 days are as follows, though almost the same form is also observed when using oat meal-agar media and yeast extract-malt extract-agar ones.

The aerial mycelium is of a linear to wave form of 0.8 to 1.0μ in diameter, and grows in simple branches to form chains of many spores. The chain of spores is of a linear to wave form, forming no spiral form. The spore is of a short column of 1.0–1.2×1.5–2.0μ in size, and its surface is smooth. The substrate mycelium, 0.5 to 0.7μ in diameter, grows in waves or in bends while forming branches, and the fission of mycelium and the generation of spore are not observed. No flagellospore nor sporangium is formed.

(II) DIAMINOPIMELIC ACID FORMATION

L-diaminopimelic acid was detected.

(III) CULTURE

The results of observation after culture at 30° C. for 20 days on various media are as shown in the table. The color is indicated according to the color classification described in Color Harmony Manual 4th edition, 1958, Container Corporation of America.

| Name of media | Growth | Conditions on Various Media Color of substrate mycelium | Aerial mycelium | Soluble coloring matter |
|---|---|---|---|---|
| Sucrose.nitrate. agar medium | Low | Colorless | Low: Oyster white (b) | None |
| Glucose.asparagine. agar medium | Moderate | Mustard Gold (2pe) | Moderate to poor: White (a) | None |
| Glycerin.asparagine. agar medium | Moderate to good | Mustard Gold (2pe) | Moderate to good: Pearl (2ba) | None |
| Starch.inorganic salt.agar medium | Moderate to good | Golden Brown (3pg) | Moderate to good: Silver Gray (3fe) to Natural (3dc) | None |
| Tyrosine.agar medium | Moderate to good | Golden Brown (3pg) | Moderate to good: Pearl (3ba) | None |
| Oatmeal.agar medium | Moderate to good | Mustard Gold (2pg) | Poor: White (a) to Pearl (3ba) | None |
| Yeast extract.malt extract.agar medium | Good | Mustard Gold (2pg) to Golden Brown (3pg) | Good: Silver Gray (3fe) to Natural (3dc) | None |
| Glycerin.nitrate. agar medium | Moderate to poor | Mustard Gold (2pg) | Poor: Pearl (3ba) | None |
| Bennett's agar medium | Moderate to good | Mustard Gold (2pg) | Moderate: Pearl (2ba) to Cream (1½ ca), partly Sand (3cb) | None |
| Emerson's agar medium | Good | Mustard Gold (2pe–2pg) | Low: White (a) | None |
| Nutrient agar medium | Poor | Light Wheat (2ea) | None | None |

(IV) PHYSIOLOGICAL PROPERTIES (1) Range of growth temperature: 10°–40° C.
(2) Liquefaction of gelatin: Positive
(3) Hydrolysis of starch: Positive
(4) Skim milk: Positive to both peptonization and coagulation.
(5) Formation of melanine-like coloring matters: Negative
(6) Utility of sugars: Positive to L-arabinose, D-fructose, D-glucose and D-xylose; negative to i-inositol, D-mannitol, raffinose, L-rhamnose and sucrose.

As described above, the A 9107 strain produces aerial mycelia having chains of many spores from the true substrate mycelia causing no fission, and also contains L-diaminopimelic acid. Judging from these facts as well as the diameter of mycelium and size of spore, the A 9107 strain shall belong to Streptomyces sp. Consequently, A 9107 strain was designated Streptomyces sp. A 9107 and has been deposited at Fermentation Research Institute, Agency of Industrial Science and Technology, Japan under FERM-P 4978, and at Agricultural Research Service, U.S. Department of Agriculture under NRRL 15100.

As the microorganism used in the present invention, there may be used not only the foregoing Streptomyces sp. A 9107, but also any of fungi belonging to genus Streptomyces and producing sphingomyelinase.

As the culture medium used in the present invention, one containing 1 to 5% of protoflour, 0.5 to 3% of corn starch, 0.1 to 0.5% of KCl, 0.1 to 0.5% of $CaCO_3$ and 0.1% of Disfoam BC-51Y, and having a pH of 7.0, is preferred. The culture is carried out at 24° to 28° C. for 40 to 50 hours with aeration and stirring. By this operation, sphingomyelinase is produced and accumulated in the culture solution.

In collecting sphingomyelinase from the culture solution after the completion of the culture and purifying it, sphingomyelinase secreted out of the mycelia can be obtained as an electrophoretically single enzyme preparation, by various operations such as salting-out with inorganic salts (e.g. ammonium sulfate), fractional precipitation with organic solvents (e.g. acetone, ethanol), adsorption chromatography with cation-exchange carriers (e.g. CM-cellulose, Sepharose, Sephadex, SP-Sephadex), molecular sieve chromatography with gel filtering agents (e.g. Sephadex G-75, G-100, Biogel P-100) and the like.

The properties of the enzyme obtained are as follows:

(1) ACTION

This enzyme acts on sphingomyelin to catalyze the reaction producing ceramide and phosphorylcholine.

(2) MEASUREMENT OF ENZYMATIC ACTIVITY

After preincubating 0.45 ml of the following reaction mixture at 37° C., 50 μl of an enzyme solution is added to start the reaction. After just 10 minutes, 0.1 ml of 0.1M EDTA is added to stop the reaction.

| | |
|---|---|
| 0.2 M Tris-HCl buffer (pH 8.0) | 0.2 ml |
| 10 mM $MgCl_2$ | 0.05 ml |
| 10 mM Sphingomyelin emulsion | 0.05 ml |
| 5% Triton X-100 | 0.05 ml |
| $H_2O$ | 0.10 ml |

The formed phosphorylcholine is led to a color development system through a $H_2O_2$ by using the following reaction mixture, and absorbance at 500 nm is measured.

| | |
|---|---|
| COD (50 μ/ml) | 0.1 ml |
| Alkaline phosphatase (40 μ/ml) | 0.1 ml |
| POD (45 μ/ml) | 0.1 ml |
| 0.3% 4-Aminoantipyrin | 0.1 ml |
| 0.2% Phenol | 0.1 ml |
| $H_2O$ | 1.9 ml |

The indication of enzymatic activity is calculated from the following equation with activity to produce 1 μmole of phosphorylcholine for 1 minute as one unit:

$$\text{Unit/ml} = \Delta A_{500\ nm} \times 0.25 \times 20 \times 1/10$$

wherein $\Delta A_{500\ nm}$ means a difference in absorbance at 500 nm between at the start of reaction and 10 minutes after the reaction.

(3) OPTIMUM pH

Enzymatic activities are measured using 0.2M dimethylglutarate-NaOH buffer (pH 5-7), 0.2M Tris-HCl buffer (pH 7.2-9) and 0.2M glycine-NaOH buffer (pH 9.5-10) in place of the Tris-HCl buffer in the reaction mixture used for the measurement of enzymatic activity. The results are shown in FIG. 1. The enzyme acts best at a pH of 7 to 8.

(4) pH STABILITY

An enzyme liquor is dissolved in 100 mM various buffers, such as dimethylglutarate-NaOH buffer (pH 5-7), Tris-HCl buffer (pH 8-9) and glycine-NaOH buffer (pH 10), so that the concentration is 26 u/ml. The enzyme solutions obtained are measured for the residual activity after treatment at 40° C. for 60 minutes. As shown in FIG. 2, the enzyme liquor is stable within a pH range of 6 to 9.

(5) THERMAL STABILITY

An enzyme solution is prepared so that its concentration in 100 mM Tris-HCl buffer (pH 7.0) is 23 u/ml, and measured for the residual activity after heated for 10 minutes at every temperatures shown on the abscissa in FIG. 3. The liquor is kept stable until the treatment at 40° C. for 10 minutes.

(6) EFFECT OF METAL IONS

| Additive | Relative activity (%) |
|---|---|
| No addition | 100 |
| 1 mM $MgCl_2$ | 232 |
| 1 mM $CaCl_2$ | 48 |
| 1 mM $MnCl_2$ | 236 |
| 1 mM $ZnCl_2$ | 3 |
| 1 mM $NiCl_2$ | 12 |
| 1 mM $BaCl_2$ | 89 |
| 1 mM $CoCl_2$ | 35 |
| 1 mM $CuCl_2$ | 19 |
| 100 mM NaCl | 73 |
| 100 mM KCl | 90 |
| 100 mM $NH_4Cl$ | 79 |

(7) EFFECT OF SURFACTANT

| Additive | Relative activity (%) |
|---|---|
| No addition | 100 |
| 0.1% Triton X-100 | 358 |
| 0.1% Adekatol SO-145 | 367 |
| 0.1% Adekatol PC-8 | 426 |
| 0.1% Adekatol L-61 | 267 |
| 0.1% Sodium deoxycholate | 16 |
| 0.1% Sodium laurylsulfate | 13 |
| 0.1% Sodium laurylbenzenesulfonate | 8 |

(8) MOLECULAR WEIGHT

It is determined by the SDS-polyacrylamide electrophoretic method using the purified enzyme. The value obtained is 36,000.

(9) ISOELECTRIC POINT

It is determined by the electrophoretic method using ampholite, a carrier. The pH obtained is 8.6.

(10) SUBSTRATE SPECIFICITY

| Additive | Relative activity (%) |
|---|---|
| Sphingomyelin | 100 |
| Lecithin | 0 |
| Lysolecithin | 0 |
| Phosphatidyl ethanolamine | 0 |
| Phosphatidyl serine | 0 |
| Phosphatidyl inositol | 0 |

Figure 1:
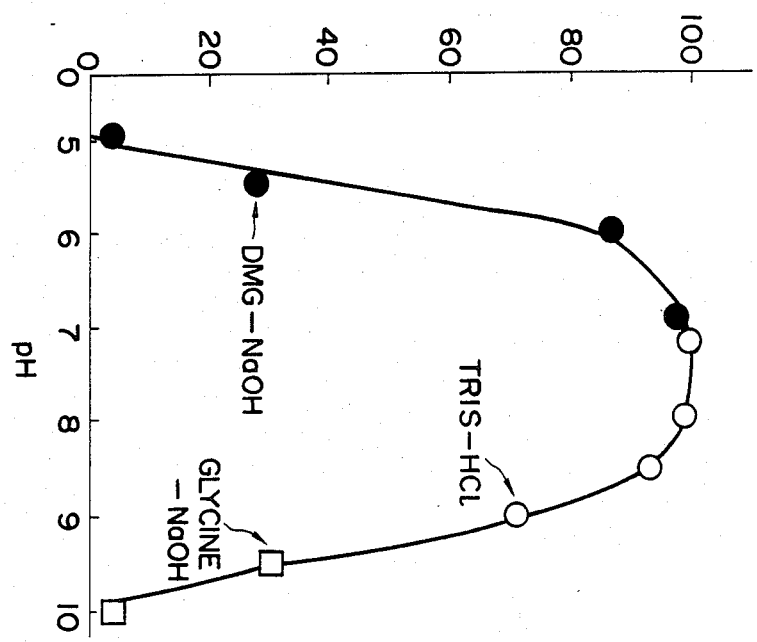
FIG. 1 is a graph showing the results of measurement of the optimum pH of sphingomyelinase obtained by the present invention.
Figure 2:
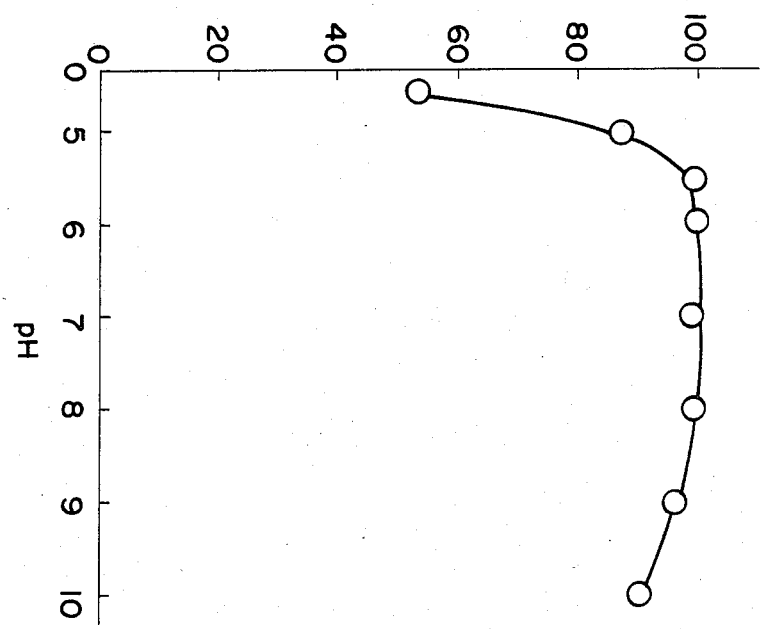
FIG. 2 is a graph showing the results of measurement of the pH stability of the same.
Figure 3:
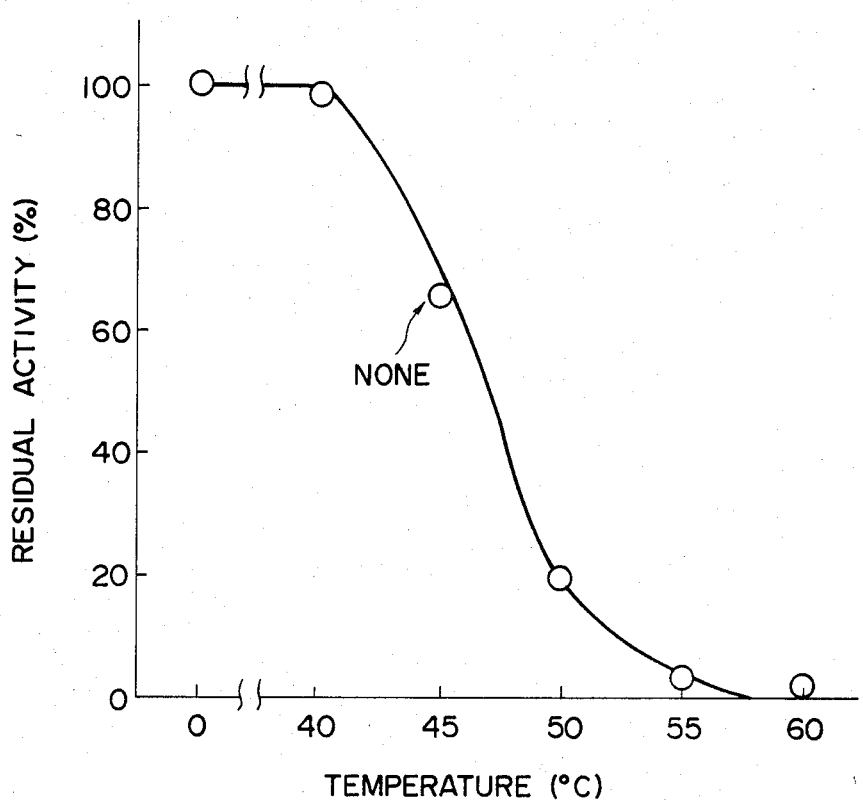
FIG. 3 is a graph showing the results of measurement of the thermal stability of the same.

Then, the present invention will be illustrated with reference to the following examples.

EXAMPLE 1

Twenty liters of a medium (pH 7.0) comprising 1.0% of protoflour, 2% of corn starch, 0.3% of KCl, 0.4% of $CaCO_3$ and 0.1% of Disfoam BC-51Y was pressure-sterilized at 120° C. for 20 minutes. After adjusting the temperature to 26° C., 400 ml of a culture solution of Streptomyces sp. A 9107 pre-cultured for 3 days in the medium of the above composition was transplanted in a 30-liter jar fermenter. Aeration/stirring culture was then carried out at 300 rpm and 20 l/min., and after 43 hours, the enzymatic titer out of the mycelia reached the maximum value (4.6 u/ml). On removing the mycelia by centrifugation at 5000 rpm for 10 minutes, 15 liters of crude sphingomycelinase solution was obtained.

EXAMPLE 2

Fifteen liters of the enzyme solution obtained by the method shown in Example 1 was concentrated to 3 liters under reduced pressure. Five liters of acetone cooled to $-20°$ C. was added to this concentrated solution to deposit the enzyme. This precipitate was dissolved in 1 liter of 10 mM Tris-HCl buffer (pH 7.5), dialyzed to 20 liters of 10 mM Tris-HCl buffer (pH 7.5) and freeze-dried to obtain 8.4 g of powder (3.8 $\mu$/mg).

EXAMPLE 3

Two point zero grams of the powder obtained by the method in Example 2 was dissolved in 50 ml of 10 mM acetate buffer (pH 5.5), and passed through a SP-Sephadex C-25 column (1.8×20 cm) buffered with the same buffer to absorb the enzyme. Thereafter, elution was carried out by the linear concentration gradient method using 250 ml of 10 mM acetate buffer and 250 ml of the buffer containing 0.2M KCl (flow rate 20 ml/hr). The activity of every fraction was measured, and the activity fractions (No. 48 to 58, 95 ml) were collected, concentrated through ultrafiltration membrane XM-50 (produced by Amicon Co.) and then passed through Sephadex G-75 column (3.0×90 cm, 10 mM dimethylglutarate buffer). The activity fractions (No. 21 to 28, 52 ml) were collected and freeze-dried to obtain 5.0 mg of purified enzyme (specific activity, 1,050 $\mu$/mg).

What is claimed is:

1. A method for the production of sphingomyelinase characterized in that the Streptomyces sp. A 9107 is cultured in a medium and the resulting sphingomyelinase is collected from the culture product.

* * * * *